US010104886B2

(12) United States Patent
Parrish

(10) Patent No.: US 10,104,886 B2
(45) **Date of Patent: *Oct. 23, 2018**

(54) MANUFACTURE AND USE OF AGRICULTURAL SPRAY ADJUVANTS FOR HARD WATER CONDITIONS

(71) Applicant: AgQuam LLC, Spokane, WA (US)

(72) Inventor: Scott K. Parrish, Spokane, WA (US)

(73) Assignee: AGQUAM LLC, Spokane, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,936

(22) Filed: Jun. 2, 2017

(65) Prior Publication Data

US 2017/0265460 A1 Sep. 21, 2017

Related U.S. Application Data

(63) Continuation of application No. 10/853,781, filed on May 26, 2004, now Pat. No. 9,668,471.

(60) Provisional application No. 60/473,540, filed on May 28, 2003.

(51) Int. Cl.
*A01N 25/10* (2006.01)
*A01N 25/22* (2006.01)
*A01N 25/32* (2006.01)

(52) U.S. Cl.
CPC ............. *A01N 25/10* (2013.01); *A01N 25/22* (2013.01); *A01N 25/32* (2013.01)

(58) Field of Classification Search
CPC ......... A01N 25/10; A01N 25/22; A01N 25/32
See application file for complete search history.

(56) References Cited

U.S. PATENT DOCUMENTS

| | | | |
|---|---|---|---|
| 6,541,424 | B2 | 4/2003 | Roberts et al. |
| 6,803,345 | B2 | 8/2004 | Herold et al. |
| 6,906,004 | B2 | 6/2005 | Parrish et al. |
| 7,094,735 | B2 | 8/2006 | Herold et al. |
| 2002/0107149 | A1 | 8/2002 | Volgas et al. |
| 2003/0144147 | A1 | 7/2003 | Herold et al. |
| 2003/0148889 | A1 | 8/2003 | Herold et al. |
| 2003/0153461 | A1 | 8/2003 | Parrish et al. |
| 2003/0153462 | A1 | 8/2003 | Herold et al. |
| 2004/0127364 | A1 | 7/2004 | Herold et al. |
| 2004/0167032 | A1 | 8/2004 | Volgas et al. |
| 2005/0170967 | A1 | 8/2005 | Parrish et al. |
| 2006/0205601 | A1 | 9/2006 | Herold et al. |

(Continued)

OTHER PUBLICATIONS

Acid Collins English Dictionary [online] retrieved on 2/24/218 from: https://www.collinsdictionary.com/dictionary/english/acid; 9 pages. (Year: 2018).*

(Continued)

*Primary Examiner* — Ernst V Arnold
(74) *Attorney, Agent, or Firm* — Swanson & Bratschun, L.L.C.

(57) ABSTRACT

The invention pertains to a method for manufacture and use of pesticides or agricultural spray adjuvants that counteracts the effects of hard water cat ions on anionic pesticides when applied in water spray solutions. The disclosed agricultural spray adjuvants include glyphosate compositions comprising a strong mineral acid, such as sulfuric acid, and a polyamine surfactant, such as tallow amine or coco amine.

5 Claims, 2 Drawing Sheets

(56) References Cited

U.S. PATENT DOCUMENTS

2006/0270557 A1 11/2006 Volgas et al.

OTHER PUBLICATIONS

Bohn et al. (1985) Soil Chemistry—Wiley Interscience $2^{nd}$ Ed. pp. 241-243.
Greenhouse Product News (1999) "Water Chemistry as it Applies to pH and Alkalinity".
Hartzler (2001) R. Extension Bulletin, Iowa State University "Role of AMS with glyphosate products".
Kessler (2005) Alabama Cooperative Extension System ANR-1158 "Water Quality Management for Greenhouse Production" (previously cited as David Wm. Reed. (1996) Water Quality Management for Greenhouse Production, Ball Publishing, Batavia, IL, ISBN: 1-883052-12-2).
Nalewaja et al. (1993) Pesticide Sci. 38:77-84 "Influence of Diammonium Sulfate and Other Salts on Glyphosate Phytotoxicity".
Petroff (2000) Pesticide Education Specialist, Montana State University Extension Service "Water Quality and Pesticide Performance".
Petroff, Pesticide Education Specialist, Montana State University Extension Service "Water Effects on Pesticide Performance".
Thelen et al. (1995) Weed Science 43(4):541-548 "The Basis for the Hard-Water Antagonism of Glyphosate Activity".

* cited by examiner

MANUFACTURE AND USE OF AGRICULTURAL SPRAY ADJUVANTS FOR HARD WATER CONDITIONS

RELATED APPLICATIONS

This application is a continuation of U.S. application Ser. No. 10/853,781, filed May 26, 2004, which issued as U.S. Pat. No. 9,668,471, on Jun. 6, 2017, which claims the benefit of U.S. Provisional Application Ser. No. 60/473,540, filed May 28, 2003, each of which is incorporated herein by reference in its entirety.

BACKGROUND

It is known that the addition of fertilizer blends in the application of many pesticides will improve the performance of the active ingredient. The current market standard is ammonium sulfate (AMS). It is speculated that one of the reasons for this is that the anion portion of the fertilizer blend, sulfate, will associate with the hard water cation. Therefore the anion or acidic pesticide will not associate with the hard water cation and be more available for uptake into the target species. "Data suggest hard-water cations, such as $Ca^{+2}$ and $Mg^{+2}$ present in the spray solution can greatly reduce the efficacy of glyphosate. These cations potentially compete with the isopropylamine in the formulation for association with the glyphosate anion."[1] Hard water with cations present in a concentration range higher than 100 ppm-150 ppm have been shown to cause a decrease in effectiveness of many pesticides.[2] It is thought by some authors that the reason for the reduced activity with glyphosate is that the glyphosate anion will form insoluble salts with many hard water cations. This would be true for many anions pesticides including glyphosate, 2,4-D and glufosinate. This would also be true for acidic herbicides that could become anionic depending upon pH an example of this would be sethoxydim.[3,4]

This information has lead to the common practice of glyphosate and other anionic pesticides being applied in the presence of ammonium sulfate (AMS) in the spray mixture. However, in other industries a common practice to remove hard water cations such as $Ca^{+2}$, $Fe^{+2}$, $Mg^{+2}$ and $Zn^{+2}$ is with acidic reaction with mineral acids such as nitric and sulfuric acid.[5] This technology has been adapted to cation management in both soil and irrigation water and is based on the "Langelier index".[6] Cation management with phosphoric acid as a spray mixture has been tried with limited success as compared to spray mixtures containing AMS. It is speculated that the reason that phosphoric acid products do not work as well as AMS is that phosphoric acid does not completely dissociate when added to water at normal spray mixture pH ranges.[8] It is therefore less reactive to the hard water cations than originally thought by the creators of these products. Other mineral acids were considered to be impractical in pesticide applications because small mistakes or misuse with these powerful acids will drop the pH of a spray solution in the spray tank below the pKa of many anionic pesticides, including glyphosate. If this occurs the pesticide will precipitate and will no longer be sprayable.

An idea was formed that mineral acid management of hard water cations would be much more efficient than AMS management of hard water cations if a mineral acid that completely dissociates in water could be used and a reliable delivery system could be devised or discovered for these types of acids. The three driving factors for this idea are: 1) Much less acid is needed to tie up the hard water cations than AMS. The amount of AMS recommended is 17.5 lb per 100 gallons of waters with 150-250 ppm hard water cations. [4] Whereas only 1.3 oz of sulfuric acid per 100 gallons is needed to neutralize the 150-250 ppm hard water cations.[7] 2) Sulfuric acid and nitric acid will form semi and insoluble salts with the hard water cations. Whereas AMS has only been shown to associate with these cations. It is unlikely that they form salts.[3] 3) AMS as a salt is hard to dissolve into the spray solutions which makes it difficult to work with. Whereas, acids are completely miscible in water.

1. The basis for the hard-water antagonism of glyphosate activity. Thelen, K. D. Weed Science v. 43 (4) 1995 pp. 541-548.

2. Weed Science Principles and Application. Anderson, WP third edition, West Publishing Co. Minneapolis, Minn.

3. Nalewaja, J. D. and R. Matysiak. 1993. Pesticide Sci. 38:77-84.

4. Role of AMS with glyphosate products. Hartzler, R. Extension Bulletin, Iowa State University.

5. David Wm. Reed. 1996. Water, media and nutrition for greenhouse crops. Ball Publishing, Batavia, Ill., ISBN: 1-883052-12-2.

6. Bohn H. L., McNeal, B. L., O'Connor, G. A., Soil Chemistry, A Wiley-Interscience Pub. John Wiley & Sons, New York, N.Y.

7. Greenhouse Product News February '99.

8. Morrison R. T. and Boyd N. B. Organic Chemistry, Allyn and Bacon, Boston, Mass.

SUMMARY OF THE INVENTION

A mixture of strong mineral acids which would completely dissociate in water, including but not limited to; nitric acid, hydrochloric acid, sulfuric acid, perchloric acid, and a polymer, preferred would be cationic, that is formulated as an agricultural spray adjuvant. The polymer in the formulation acts as a slow release mechanism for the acid. Polymeric forces on the mineral acid give the grower a practical mechanism for using mineral acid to counteract hard water cations. The adjuvant when mixed in a agricultural spray solution would act to tie up the hard water cations thus protecting any anionic pesticides, defoliants or plant growth regulators from reacting with the hard water cations such as $Ca^{++}$, $Mg^{++}$, $Fe^{++}$ and becoming less effective as an agricultural chemicals. Thus the spray adjuvant would act to increase the apparent efficacy of the active ingredient being applied.

DETAILED DESCRIPTION OF THE INVENTION

Strong mineral acids were added to polymers in an attempt to deliver a controlled amount of acid into a spray solution. The acid would act as a "hard water cation scavenger". The mixture would be an agronomic spray "hard water scavenger system". In the preferred example sulfuric acid was added to tallow amine. Heat was given off indicating some reaction. However, pH measurements of spray mixtures taken before and after the addition of the "hard water scavenger system" shows that free acid still existed.

Knowing that any potential spray solution which could be contemplated would have to stay above a pH of which is higher than the pKa of most anionic pesticides. Differing mixtures of several examples where made up. Table 1, Table 2, Table 3. It was thought that this would be a more efficient method to condition the spray waters than current practice of using Ammonium Sulfate (AMS). However, the mixture would have to remain stable, not drop the pH below the pKa of anionic pesticides and work as well as or better than AMS. The efficiency would be gained by replacing large bags of dry AMS (17.5 lbs/100 gallons spray solution) or large volumes (5 gallon/100 gallons spray solution) of liquid AMS with 1 quart to 1 gallon per 100 gallons of spray solution with this kind of product. Also this liquid product would go into solution much faster than the current AMS goes into solution adding even more efficiency.

It was discovered that cationic macro molecules would make a stable mix with sulfuric acid. Also, cationic surfactant would act as a system that would deliver enough free acid to tie up hard water cations. While at the same time maintain the pH of the spray water above the pKa of the active ingredient being sprayed thus increasing the efficacy of the pesticide.

Figure 1:
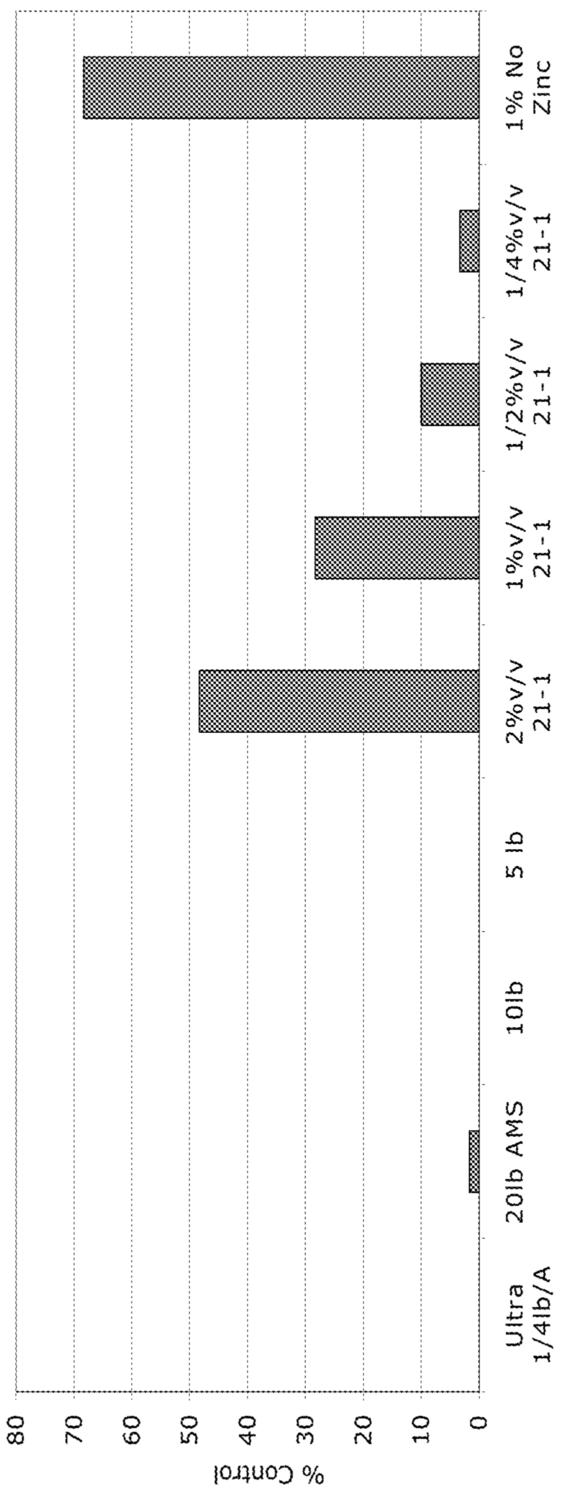
FIG. 1. Formula 21-1 as compared to AMS for the reduction of hard water tie up of glyphosate salt. As measured by percent control of annual bluegrass. Zinc acetate added as the complexing Anion. V/v=volume to volume.
Figure 2:
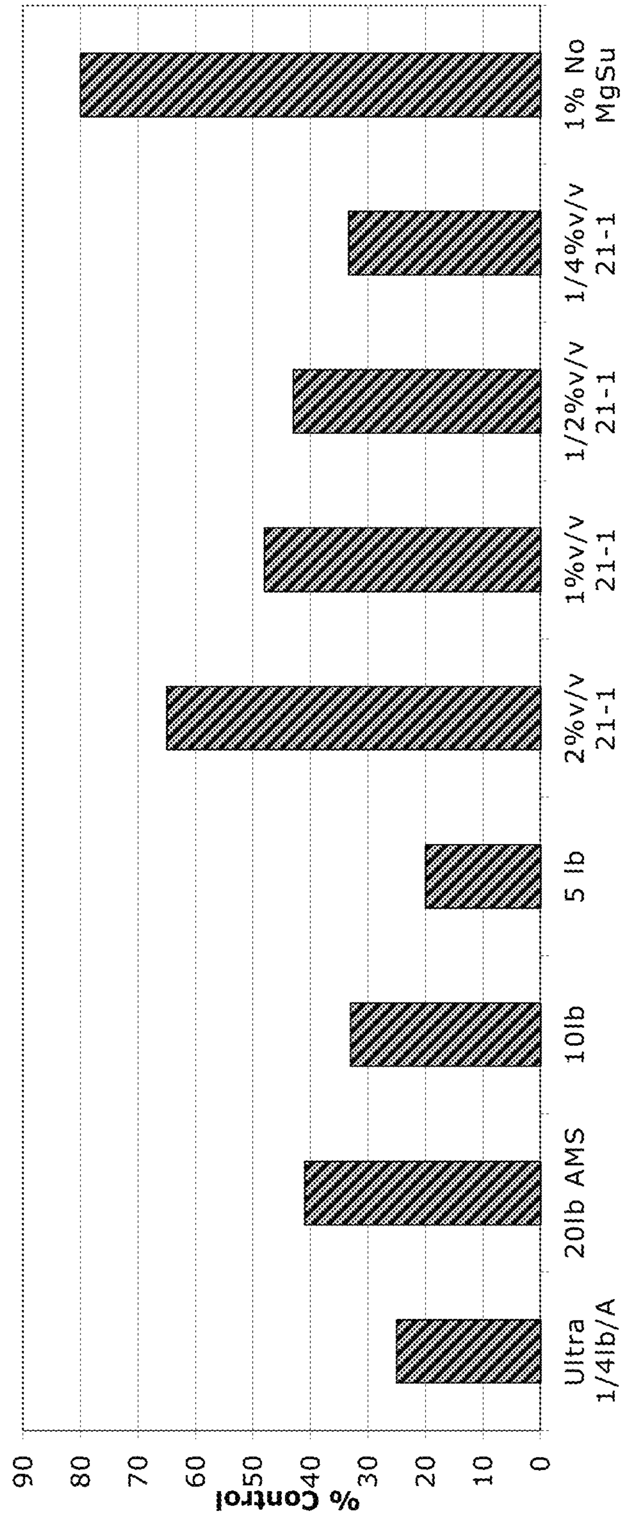
FIG. 2. The effect of Formula 21-1 on restoring the activity of glyphosate as demonstrated by percent control of annual bluegrass as compared to ammonium sulfate (AMS). Magnesium Sulfant (MgSu) was added to the mixture to simulate hard water cations.

It was surprising to discover that these mixtures increased or maintained the efficacy of anionic pesticides under hard water conditions much better than the current practice of adding Ammonium Sulfate (FIG. 1 and FIG. 2).

TABLE 1

| Example 1<br>Formula 21-1 | |
|---|---|
| Water | 65.9%/wt |
| Tallow Am 3780 | 30.0 |
| SAG 10 | 0.1 |
| 93% Sulfuric | 4.0 |

TABLE 2

| Example 2<br>Formula 21-2 | |
|---|---|
| Water | 45.9%/wt |
| Tallow Am 3780 | 50.0 |
| SAG10 | 0.1 |
| 93% Sulfuric | 4.0 |

TABLE 3

| Example 3 | |
|---|---|
| INGREDIENT | %/WT |
| Diethylene Glycol | 17.80 |
| NP-10 | 50.00 |
| AU391 | 30.00 |
| 93% Sulfuric Acid | 2.00 |
| SAG 10 [ | 0.20 |

What is claimed is:

1. A water soluble glyphosate composition comprising:

(a) an aqueous glyphosate solution comprising glyphosate or a salt thereof; (b) a concentrated solution comprising sulfuric acid and a polyamine surfactant selected from tallow amine ethoxylate and coco amine ethoxylate combined in an agricultural spray solution;

wherein said composition does not contain ammonium sulfate (AMS); and wherein said composition consists of a ratio of 1 quart to 2 gallons of (b) to 100 gallons of (a);

and wherein said composition has a pH above the $PKa_2$ of glyphosate, and wherein better herbicidal efficacy is provided in comparison to 5-20 pounds AMS per 100 gallons of (a).

2. The composition as claimed in claim 1, wherein said polyamine surfactant is tallow amine ethoxylate.

3. The composition as claimed in claim 1, wherein said polyamine surfactant is coco amine ethoxylate.

4. A water soluble glyphosate composition of claim 1 wherein said composition consists of a ratio of 1 quart to 1 gallon of (b) to 100 gallons of (a).

5. The composition as claimed in claim 1, further comprising sodium bisulfate.

* * * * *